(12) United States Patent
Newell et al.

(10) Patent No.: US 9,901,472 B2
(45) Date of Patent: *Feb. 27, 2018

(54) METHODS AND APPARATUS FOR LUMINAL STENTING

(71) Applicant: Covidien LP, Mansfield, MA (US)

(72) Inventors: Gabriel Newell, San Francisco, CA (US); Andy Huynh, Westminster, CA (US); Lawrence Farhat, Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/073,079

(22) Filed: Mar. 17, 2016

(65) Prior Publication Data

US 2016/0193061 A1    Jul. 7, 2016

Related U.S. Application Data

(63) Continuation of application No. 13/795,556, filed on Mar. 12, 2013, now Pat. No. 9,295,571.

(60) Provisional application No. 61/753,533, filed on Jan. 17, 2013.

(51) Int. Cl.
| | |
|---|---|
| *A61F 2/966* | (2013.01) |
| *A61F 2/844* | (2013.01) |
| *A61F 2/95* | (2013.01) |
| *A61B 17/12* | (2006.01) |

(52) U.S. Cl.
CPC ............ *A61F 2/966* (2013.01); *A61F 2/844* (2013.01); *A61B 2017/1205* (2013.01); *A61F 2002/9534* (2013.01); *A61F 2002/9665* (2013.01); *A61F 2210/0014* (2013.01)

(58) Field of Classification Search
CPC .............. A61F 2/966; A61F 2002/9528; A61F 2002/9522; A61F 2/95; A61F 2002/9505; A61F 2002/9511; A61F 2/958; A61F 2002/9583; A61F 2002/9586; A61F 2/962; A61F 2/2439; A61F 2/2436; A61F 2/243; A61F 2/2427; A61F 2/2466; A61B 2017/1205

See application file for complete search history.

(56) References Cited

U.S. PATENT DOCUMENTS

| | | |
|---|---|---|
| 3,108,593 A | 10/1963 | Glassman |
| 4,425,908 A | 1/1984 | Simon |
| 4,619,246 A | 10/1986 | Molgaard-Nielsen et al. |
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsanti |
| 5,026,377 A | 6/1991 | Burton et al. |
| 5,061,275 A | 10/1991 | Wallsten et al. |
| 5,064,435 A | 11/1991 | Porter |

(Continued)

*Primary Examiner* — Tuan V Nguyen
*Assistant Examiner* — Chima Igboko
(74) *Attorney, Agent, or Firm* — Fortem IP LLP; Matthew Lincicum

(57) ABSTRACT

A stent delivery system can include a core wire and a self-expanding member disposed along the core wire. The self-expanding member can be used to facilitate expansion of a stent or other implantable device within the vasculature of a patient. The self-expanding member can include first and second end portions that are each axially slidable along the core wire and be able to expand from a collapsed configuration to an expanded configuration upon axial convergence of the first and second end portions.

18 Claims, 6 Drawing Sheets

(56) References Cited

U.S. PATENT DOCUMENTS

| | | |
|---|---|---|
| 5,104,404 A | 4/1992 | Wolff |
| 5,122,136 A | 6/1992 | Guglielmi et al. |
| 5,158,548 A | 10/1992 | Lau et al. |
| 5,222,971 A | 6/1993 | Willard et al. |
| 5,250,071 A | 10/1993 | Palermo |
| 5,308,356 A | 5/1994 | Blackshear, Jr. et al. |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,484,444 A | 1/1996 | Braunschweiler et al. |
| 5,499,981 A | 3/1996 | Kordis |
| 5,527,338 A | 6/1996 | Purdy |
| 5,545,208 A | 8/1996 | Wolff et al. |
| 5,545,209 A | 8/1996 | Roberts et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,662,703 A | 9/1997 | Yurek et al. |
| 5,690,671 A | 11/1997 | McGurk et al. |
| 5,702,419 A | 12/1997 | Berry et al. |
| 5,713,907 A | 2/1998 | Hogendijk et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,853,422 A | 12/1998 | Huebsch et al. |
| 5,855,578 A | 1/1999 | Guglielmi et al. |
| 5,879,366 A | 3/1999 | Shaw et al. |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,976,162 A | 11/1999 | Doan et al. |
| 5,980,554 A | 11/1999 | Lenker et al. |
| 6,001,092 A | 12/1999 | Mirigian et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,059,813 A | 5/2000 | Vrba et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,106,530 A | 8/2000 | Harada |
| 6,110,191 A | 8/2000 | Dehdashtian et al. |
| 6,123,715 A | 9/2000 | Amplatz |
| 6,139,564 A | 10/2000 | Teoh |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,280,412 B1 | 8/2001 | Pederson, Jr. et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 | 3/2002 | Hieshima et al. |
| 6,368,339 B1 | 4/2002 | Amplatz |
| 6,375,668 B1 | 4/2002 | Gifford et al. |
| 6,379,372 B1 | 4/2002 | Dehdashtian et al. |
| 6,383,174 B1 | 5/2002 | Eder |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 | 9/2002 | Bosma et al. |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 | 3/2003 | Jacobsen et al. |
| 6,544,278 B1 | 4/2003 | Vrba et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,302 B2 | 6/2003 | Duerig et al. |
| 6,579,303 B2 | 6/2003 | Amplatz |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,592,605 B2 | 7/2003 | Lenker et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | VanTassel et al. |
| 6,652,556 B1 | 11/2003 | VanTassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,709,465 B2 | 3/2004 | Mitchell et al. |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |

(56) References Cited

U.S. PATENT DOCUMENTS

| | | |
|---|---|---|
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | van der Burg et al. |
| 6,994,717 B2 | 2/2006 | Konya et al. |
| 7,011,671 B2 | 3/2006 | Welch |
| 7,018,401 B1 | 3/2006 | Hyodoh et al. |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 8,454,681 B2 | 6/2013 | Holman et al. |
| 9,179,918 B2 | 11/2015 | Levy et al. |
| 2001/0000797 A1 | 5/2001 | Mazzocchi |
| 2001/0007082 A1 | 7/2001 | Dusbabek et al. |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0111647 A1 | 8/2002 | Khairkhahan et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1 | 10/2004 | Coyle |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0222605 A1 | 10/2005 | Greenhalgh et al. |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0041269 A1* | 2/2006 | Horrigan .......... A61B 17/12036 606/198 |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |

(56) References Cited

U.S. PATENT DOCUMENTS

| | | |
|---|---|---|
| 2006/0217799 A1 | 9/2006 | Mailander et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von Oepen et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1 | 12/2009 | Linder et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030220 A1 | 2/2010 | Truckai et al. |
| 2010/0036390 A1 | 2/2010 | Gumm |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0222802 A1 | 9/2010 | Gillespie, Jr. et al. |
| 2010/0249894 A1 | 9/2010 | Oba et al. |
| 2010/0256667 A1 | 10/2010 | Ashby et al. |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |

(56) References Cited

U.S. PATENT DOCUMENTS

| | | |
|---|---|---|
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2014/0128905 A1 | 5/2014 | Molaei |
| 2014/0172001 A1 | 6/2014 | Becking et al. |
| 2014/0200648 A1 | 7/2014 | Newell et al. |
| 2014/0277361 A1 | 9/2014 | Farhat et al. |
| 2015/0157331 A1 | 6/2015 | Levy et al. |
| 2015/0245932 A1 | 9/2015 | Molaei et al. |
| 2016/0015395 A1 | 1/2016 | Molaei et al. |
| 2016/0113786 A1 | 4/2016 | Levy et al. |

\* cited by examiner

METHODS AND APPARATUS FOR LUMINAL STENTING

CROSS-REFERENCE TO RELATED APPLICATIONS

This application is a continuation of U.S. patent application Ser. No. 13/795,556, filed on Mar. 12, 2013, which claims priority to U.S. Provisional Patent Application No. 61/753,533, filed on Jan. 17, 2013, the entireties of each of which are incorporated herein by reference.

BACKGROUND

Field

The present application generally relates to implantable devices for use within a patient's body and, more particularly, relates to methods for implanting devices, such as stents, in a patient's body and monitoring an occlusion.

Description of the Related Art

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, a ruptured aneurysm can also result in death.

SUMMARY

At least one aspect of the disclosure provides methods for implanting a device or devices (e.g., stent or stents) in the body. The device can easily conform to the shape of the tortuous vessels of the vasculature. The device can direct the blood flow within a vessel away from an aneurysm. Additionally, such a device can allow adequate blood flow to be provided to adjacent structures, such that those structures, whether they are branch vessels or oxygen demanding tissues, are not deprived of the necessary blood flow.

In accordance with some embodiments, a stent delivery system is provided that can comprise an elongate body, a stent, a core wire, and an expandable member. The elongate body can comprise a distal portion, a proximal portion, and an inner surface extending from the distal portion to the proximal portion. The distal portion can be configured to extend within a blood vessel of a patient. The stent can be expandable from a compressed configuration to an expanded configuration. The stent can have a proximal end, a distal end, an inner surface, and an outer surface. The inner and outer surfaces can extend from the proximal end to the distal end. The core wire can be extensible through the elongate body and the stent can have a distal region or terminal portion. The expandable member can be disposed along the core wire. The expandable member can be configured to facilitate the expansion of at least a portion of the stent to the expanded configuration by expanding and engaging the inner surface of the stent.

In some embodiments, the expandable member can comprise first and second ends that are rotatably and slidably movable relative to the core wire. The expandable member can be positioned proximally of the stent proximal end when the stent is in the compressed configuration. However, the expandable member can be positioned within a lumen of the stent when the stent is in the compressed configuration. The delivery system can further comprise at least one blocking member disposed along the core wire. The blocking member can be configured to limit the movement of the expandable member relative to the core wire. Further, the clinician can push or withdraw the core wire until the blocking member(s) contact(s) the expandable member, whereupon further pushing or withdrawing of the core wire allows the clinician to push or withdraw the expandable member.

In accordance with some embodiments, the blocking member(s) can engage with a distal end of the expandable member to push the expandable member distally. The blocking member(s) can also engage with a proximal end of the expandable member to withdraw the expandable member proximally. For example, the blocking member(s) can be disposed along the core wire between expandable member first and second ends, and the blocking member(s) can have an outer cross-sectional profile that is greater than an inner cross-sectional profile of the lumens of the expandable member first and second ends. Further, in such embodiments, the blocking member(s) can be a fixed blocking member. In some embodiments, the fixed blocking member can be fixed to the core wire.

Thus, in some embodiments, the expandable member can be moved proximally or distally without axially compressing the proximal and distal ends of the expandable member, which could cause the expandable member to invert or become jammed inside of the stent lumen.

For example, the at least one blocking member can comprise at least one fixed blocking member. The fixed blocking member can be fixed to the core wire. The fixed blocking member can define an outer profile or cross-section that is greater than an inner profile or cross-section of a lumen of the movable blocking member. Accordingly, one or more fixed blocking members can be positioned along the core wire and interact with one and/or both of the ends of the expandable member to limit the travel thereof.

In some embodiments, the at least one blocking member can comprise at least one fixed blocking member and at least one movable blocking member. In such embodiments, the movable blocking member can define an outer profile or cross-section that is greater than an inner profile or cross-section of a lumen of an end of the expandable member. Further, the movable blocking member can have a lumen that defines an inner profile or cross-section section that is less than an outer profile or cross-section of a fixed blocking member disposed along the core wire. The movable blocking member can be disposed between an end of the expandable member and the fixed blocking member. Thus, the end of the expandable member can be blocked from sliding past the movable blocking member and the fixed blocking member.

The expandable member can be configured to comprise a plurality of filaments extending from a first end to a second end thereof. Further, the expandable member can comprise a shape memory material. The expandable member can self-expand upon being unsheathed from a microcatheter, e.g., when radially unrestrained by the elongate body.

The system can also optionally comprise a distal stent cover extending proximally from the distal region of the core wire and interposed between the outer surface of the stent and the inner surface of the elongate member. The distal stent cover can comprise a folded region having (a) an outer layer configured to be urged against the inner surface of the elongate member and (b) an inner layer configured to contact the outer surface of the stent. Further, the folded region can be an inverted section of the distal stent cover where the distal stent cover folds within itself. The distal stent cover can be coupled to the core wire. Further, the distal stent cover can be formed by one or more flaps of material. The distal stent cover can also comprise a lubricious material.

The system can further comprise an atraumatic tip coil coupled to the distal region of the core wire. For example, the distal stent cover can be coupled to the tip coil. Further, the distal stent cover can be coupled to the tip coil by a shrink tube.

In accordance with some embodiments, a method of deploying a stent in a vessel of a patient is also provided. The method can include extending an elongate body within the vessel of the patient, the elongate body having an inner surface extending from a distal portion to a proximal portion of the elongate body; extending within the elongate body a core assembly having an expandable member and an expandable stent having an inner surface and a distal end; advancing, relative to and within the elongate body, the core assembly, wherein the stent and the expandable member are in a compressed configuration and the stent at least partially covers the expandable member; and expanding the expandable member and engaging the stent inner surface with the expandable member when at least the distal end of the stent is expanded. Expansion of the expandable member can contribute to the expansion of the stent by engaging an inner surface of the stent.

The method can be performed such that the advancing the expandable member with the stent comprises permitting expansion of the distal end of the stent using the expandable member upon being unsheathed from the distal portion of the elongate body, e.g., when radially unrestrained by the elongate body. The method can also be performed such that expanding of the expandable member comprises allowing the expandable member to self-expand or automatically expand when radially unrestrained by the elongate body.

The method can also comprise axially moving the expandable member within a lumen of the stent to facilitate expansion of at least a portion of the stent. The method can be performed such that axially moving the expandable member comprises axially moving the expandable member in proximal and distal directions within the lumen of the stent. The method can be performed such that axially moving the expandable member comprises preventing the expandable member from moving axially beyond the stent distal end. Further, the method can also be performed such that axially moving the expandable member comprises proximally withdrawing the expandable member within the stent lumen. Furthermore, the method can also be performed such that axially moving the expandable member comprises distally pushing the expandable member within the stent lumen.

In some embodiments, the core assembly can also comprise a distal stent cover. The distal stent cover can extend proximally from a distal region of a core wire extending through the stent and be interposed between an outer surface of the stent and the inner surface of the elongate member. In such embodiments, the method can further comprise advancing the core assembly out of the distal portion of the elongate body, such that the distal stent cover withdraws from the distal end of the stent as the stent expands.

The method can be performed such that the distal stent cover of the stent is extended in the elongate body with a proximal portion of the distal stent cover being inverted to form a folded region having an outer layer configured to be urged against the inner surface of the elongate member and an inner layer configured to contact the outer surface of the stent. Further, the method can also be performed such that the distal stent cover withdraws from the distal end. The folded region can be unfurled from between the inner surface of the elongate member and the outer surface of the stent. For example, in some embodiments, ends of the folded region can be inverted within the distal stent cover, such that the end of the distal stent cover forms the inner layer/surface between the outer surface of the stent and the distal stent cover. This can permit distal advancement of the core wire assembly through the catheter, while engaging the inner surface of the catheter, without unfurling. In addition, the distal stent cover can provide a lubricious interface between the distal end and the inner surface of the elongate member. For example, the distal stent cover can have a coefficient of friction of between about 0.02 and about 0.2. In some embodiments, the distal stent cover can have a coefficient of friction of about 0.04.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It should be noted, however, that the subject technology may be practiced without some of these specific details. In other instances, well-known structures and techniques have not been shown in detail so as not to obscure the subject technology.

A discussion of aneurysm treatment technology, treatment methods (including delivery methods), and various delivery devices and stents, is disclosed in U.S. patent application Ser. No. 13/614,349, titled Methods and Apparatus for Luminal Stenting, filed on Sep. 13, 2012, the entirety of which is incorporated herein by reference.

Stents for use in practicing the technology disclosed herein can be configured to comprise one or more of a variety of structures and/or vascular devices, such as stent grafts, tubular embolization devices, braided implants, laser cut implants, scrolled implants, and other various implantable support, revascularization, and/or occluding devices. Further, in some embodiments, "occluding device" and "stent" as used herein can be used interchangeably. In some embodiments, "cell" and "pore" as used herein can be used interchangeably. In some embodiments, porosity refers to a value inversely proportional to lattice density.

Figure 1:
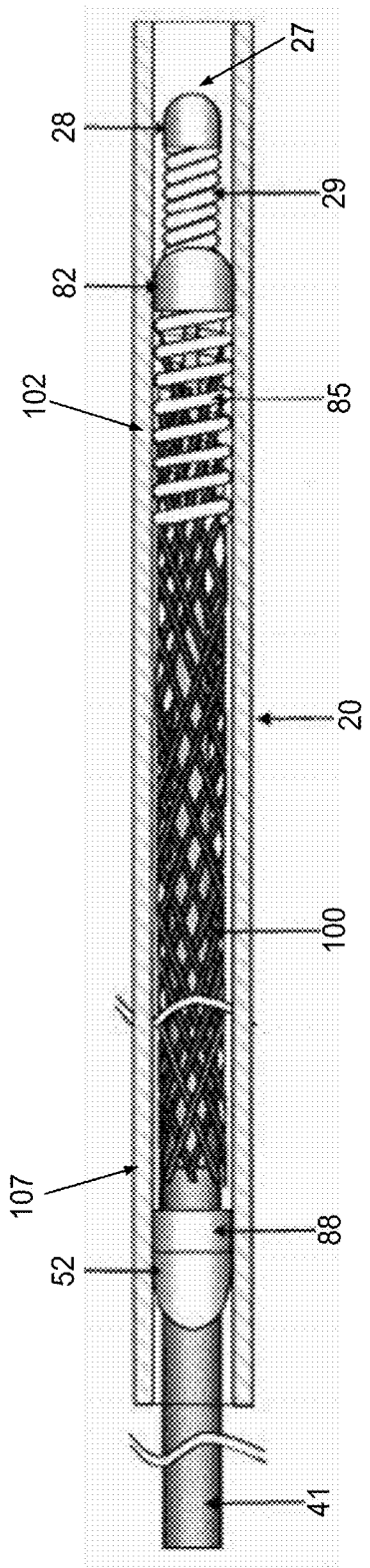
FIG. 1 is a partial cross-sectional view of an exemplary stent delivery system, according to one or more embodiments disclosed.

Described herein are various embodiments of stent delivery systems which can exhibit small cross-sections and/or be highly flexible. Referring to FIG. 1, an embodiment of a stent delivery system 20 is shown including a stent 100 carried by a core wire 41 arranged within an introducer sheath or catheter 4. The stent delivery system 20 is shown in a pre-deployment, unexpanded, or collapsed state. The stent 100 and the core wire 41 can be cooperatively movable within the catheter 4 in order to deliver the stent 100 to a predetermined treatment site, such as an aneurysm, within the vasculature of a patient. Accordingly, the catheter 4 can be configured to be introduced and advanced through the vasculature of the patient. The catheter 4 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter 4 or an adjacent surface with a hydrophilic material such as polyvinylpyrrolidone (PVP) or some other plastic coating. Additionally, either surface can be coated with various combinations of different materials, depending upon the desired results.

Information regarding additional embodiments, features, and other details of the occlusion devices or stents, methods of use, and other components that can optionally be used or implemented in embodiments of the occlusion devices or stents described herein, can be found in U.S. patent application Ser. No. 13/614,349, titled Methods and Apparatus for Luminal Stenting, filed on Sep. 13, 2012, the entirety of which is incorporated herein by reference.

The stent 100 can be characterized as a vascular occluding device, a revascularization device and/or an embolization device. The stent 100 can comprise a proximal end and a distal end. The stent 100 can comprise a braided stent or other form of stent such as a laser-cut stent, roll-up stent, etc. In some embodiments, the stent 100 can be an expandable stent made of two or more filaments. The filaments can be formed of known flexible materials including shape memory materials, such as nitinol, platinum and stainless steel. In some embodiments, the filaments can be round or ovoid wire. Further, the filaments can be configured such that the stent is self-expanding. In some embodiments, the stent 100 is fabricated from platinum/8% tungsten and 35N LT (cobalt nickel alloy, which is a low titanium version of MP35N alloy) alloy wires. In some embodiments, one or more of the filaments can be formed of a biocompatible metal material or a biocompatible polymer.

The stent 100 can optionally be configured to act as a "flow diverter" device for treatment of aneurysms, such as those found in blood vessels including arteries in the brain or within the cranium, or in other locations in the body such as peripheral arteries. The stent 100 can optionally be similar to any of the versions or sizes of the PIPELINE™ Embolization Device marketed by Covidien of Mansfield, Mass. USA. The stent 100 can further alternatively comprise any suitable tubular medical device and/or other features, as described herein.

The wire filaments can be braided into a resulting lattice-like structure. In some embodiments, during braiding or winding of the stent 100, the filaments can be loosely braided using a 1-over-2-under-2 pattern. In other embodiments, however, other methods of braiding can be followed, without departing from the scope of the disclosure. The stent 100 can exhibit a porosity configured to reduce haemodynamic flow into, for example, an aneurysm, but simultaneously allow perfusion to an adjacent branch vessel. As will be appreciated, the porosity of the stent 100 can be adjusted by "packing" the stent during deployment, as known in the art. The ends of the stent 100 can be cut to length and therefore remain free for radial expansion and contraction. The stent 100 can exhibit a high degree of flexibility due to the materials used, the density (i.e., the porosity) of the filaments, and the fact that the ends are not secured.

The flexibility of the core wire 41 allows the stent delivery system 20 to bend and conform to the curvature of the vasculature as needed for positional movement of the stent 100 within the vasculature. The core wire 41 can be made of a conventional guidewire material and have a solid cross-section. Alternatively, the core wire 41 can be formed from a hypotube. The material used for the core wire 41 can be any of the known guidewire materials including superelastic metals or shape memory alloys, e.g., nitinol. Alternatively, the core wire 41 can be formed of metals such as stainless steel.

In one or more embodiments, the stent delivery system 20 can exhibit the same degree of flexion along its entire length. In other embodiments, however, the stent delivery system 20 can have two or more longitudinal sections, each with differing degrees of flexion or stiffness. The different degrees of flexions for the stent delivery system 20 can be created using different materials and/or thicknesses within different longitudinal sections of the core wire 41. In another embodiment, the flexion of the core wire 41 can be controlled by spaced cuts (not shown) formed within the core wire 41. These cuts can be longitudinally and/or circumferentially spaced from each other.

A tip 28 and flexible tip coil 29 can be secured to the distal end 27 of the core wire 41. The tip 28 can be characterized as a distal solder joint formed of a continuous end cap or cover as shown in the figures, which securely receives or is embedded in a distal end of the tip coil 29. Flexion control is provided to the distal end 27 of the core wire 41 by the tip coil 29. However, in some embodiments, the tip 28 can be free of the coil 29. As illustrated, the tip 28 can have a non-puncturing, atraumatic end face. The tip coil 29 can be configured to surround at least a portion of the core wire 41. The tip coil 29 is flexible so that it will conform to and follow the path of a vessel within the patient as the tip 28 is advanced along the vessel and the core wire 41 bends to follow the tortuous path of the vasculature.

At the proximal end 107 of the stent 100, a proximal solder joint 52 and proximal marker 88 prevent or limit longitudinal movement of the stent 100 along the length of the core wire 41 in the direction of the proximal end 107. As illustrated, the proximal end 107 of the stent 100 can be axially offset from the proximal marker 88 by a short distance. In other embodiments, however, the stent 100 can shift axially during introduction into the vasculature of the patient and contact the proximal marker 88 which prevents or limits the stent 100 from moving along the length of the core wire 41 away from a distally located protective coil 85 coupled to an adjacent or mid solder joint 82.

After navigating the length of the catheter 4 to the predetermined treatment site within the patient, the stent 100 can be deployed from the catheter 4 in a variety of ways. In some embodiments, the catheter 4 is retracted while maintaining the position of the core wire 41 to expose the distal end 27 of the core wire 41 and the distal end 102 of the stent 100. Upon exiting the catheter 4, the portion of the stent 100 that is not situated between the protective coil 85 and the core wire 41 and that is not covered by the catheter 4 begins to expand radially. The catheter 4 can then be further retracted until enough of the stent 100 is exposed, such that the expansion diameter of the stent 100 is sufficient to engage the walls of the vessel (not shown), such as a blood vessel. Upon engaging a portion of said vessel, the stent 100 can be at least partially anchored within the vessel.

The core wire 41 can then be rotated at its proximal end, which causes rotation at the distal end 27 relative to the stent 100. The rotation of the core wire 41 also causes twisting of the protective coil 85, which pushes the distal end 102 of the stent 100 out from beneath the protective coil 85 like a corkscrew. Once the distal end 102 of the stent 100 is released from the protective coil 85, it expands to engage the walls of the vessel. The catheter 4 can then be further retracted to expose and expand the remaining portions of the stent 100 into engagement with the blood vessel wall.

Variations of this deployment method are possible. For example, the catheter 4 can be further retracted before rotating the core wire 41, thereby expanding the proximal end 107 of the stent 100 before expanding the distal end 102. Other examples of deployment variations include causing or otherwise creating variable porosity of the stent 100.

Once the entire stent 100 is expanded, the core wire 41 can then be retracted back into the catheter 4 by pulling proximally on the core wire 41 and maintaining the catheter 4 in its position. The proximal taper of the solder joint 52 coupled to the proximal marker 88 helps guide retraction of the core wire 41 back into the catheter 4. The core wire 41 and the catheter 4 can then be both retracted from the vessel and vasculature of the patient.

Figure 2:
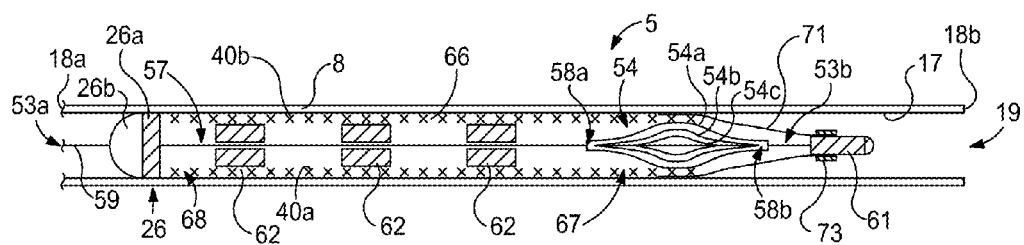
FIG. 2 illustrates a cross-sectional view of an exemplary stent delivery system, according to one or more embodiments disclosed.

Referring now to FIG. 2, illustrated is a cross-sectional view of another embodiment of a stent delivery system 5, according to one or more embodiments disclosed. The system 5 can include an elongate body, such as a catheter 8, a core assembly 57 extending generally longitudinally through the catheter 8 (e.g., a microcatheter), and a stent 66 loaded onto the core assembly 57. The elongate body or catheter 8 can define a lumen extending therethrough from a proximal portion to a distal portion thereof. The core assembly 57 can be slidably received within the catheter 8 and used to deploy the stent 66 in a lumen, such as the blood vessel 69 shown in FIGS. 5-9.

In some embodiments, the stent 66 can be a self-expanding stent. However, the stent 66 can also be configured to be expanded using other means, such as a balloon and the like. The stent 66 can, in various embodiments, be similar to any of the embodiments of the stent 100 disclosed herein.

The stent 66 can define a lumen extending therethrough and include an inner surface 40*a*, an outer surface 40*b*, a distal end 67, and a proximal end 68. The stent 66 can be loaded onto the core assembly 57 in a compressed configuration within the catheter 8, as shown in FIG. 2. In one or more embodiments, the stent 66 is maintained in its compressed configuration within the catheter 8 by an inner surface 17 of the catheter 8. Some embodiments of the stent 66 can be configured to automatically expand or self-expand radially from its compressed configuration to its expanded configuration as the stent 66 is deployed from the catheter 8 and into a blood vessel, as discussed in more detail below.

The elongate body or catheter 8 can extend longitudinally from a proximal portion 18*a* to a distal portion 18*b*. At the distal portion 18*b*, the catheter 8 defines a distal opening 19 through which the core assembly 57 can be advanced beyond the distal portion 18*b* in order to deploy the stent 66 within the blood vessel. A proximal opening (not shown) is defined at the opposing end of the catheter 8 through which the core assembly 57 can be initially inserted into the catheter 8.

As illustrated in FIG. 2, the core assembly 57 includes a core wire 59 or other core member as disclosed herein extending generally longitudinally through a lumen of the catheter 8 and terminating at a flexible tip coil 61. In particular, the core wire 59 has a proximal end 53*a* and a terminal or distal end 53*b*, and the tip coil 61 can be coupled to the distal (terminal) end 53*b* of the core wire 59. In some embodiments, the tip coil 61 can be substantially similar to the tip 28 and tip coil 29 combination described above with reference to FIG. 1, and the core wire 59 can be substantially similar to the core wire 41, also described above with reference to FIG. 1. The tip coil 61 can have an atraumatic end face, such as a rounded or smoothed face. In other embodiments, the tip coil 61 can have other atraumatic shapes designed to prevent injury to the vessel into which it can be introduced.

The core wire 59 can be sufficiently flexible to allow flexure and bend as it traverses tortuous vessels. Moreover, the core wire 59 can be secured to the tip coil 61, such that the tip coil 61 is able to be translated within the catheter 8 and/or a blood vessel by manipulating the axial position of the core wire 59. In some embodiments, the core wire 59 is configured to transmit torque and axial or longitudinal force from the proximal end 53*a* of the core wire 59 through the distal end 53*b* to the tip coil 61.

The core assembly 57 can also include a proximal retaining member or proximal bumper 26 and one or more stent bumpers or pads 62. The proximal retaining member 26 can be spaced proximally from the tip coil 61. Further, the proximal retaining member 26 can be concentrically disposed within the catheter 8. Additionally, the proximal retaining member 26 can define a width or diameter that is approximately equal to an inside diameter of the lumen of the catheter 8. However, the width or diameter of the proximal retaining member 26 can be much less than the inside diameter of the lumen of the catheter 8. The proximal retaining member 26 can be generally circular or cylindrical in shape. However, the proximal retaining member 26 can also define other geometries, such as square, rectangular, triangular, or have other features that can be configured to interact with the stent 66 in a manner providing a proximal limit or boundary. Thus, the proximal retaining member 26 can comprise a core connector and one or more stent abutment portions extending from the core connector that can contact the stent 66 to provide a proximal limit or boundary.

The proximal retaining member 26 can comprise a radiopaque marker to facilitate the locating and viewing of the core assembly 57 in the blood vessel. For example, the proximal retaining member or bumper 26 can comprise a marker band 26*a* fixed to the core wire 59 via a solder bead 26*b*. The marker band 26*a* can be a generally cylindrical structure made of platinum or other radiopaque material. In some embodiments, the proximal bumper 26 can be arranged in the core assembly 59, such that there is a small gap defined between the proximal bumper 26 and the stent 66. For example, in some embodiments, a gap ranging between about 0.0 mm to about 0.5 mm can be defined between the proximal bumper 26 and the stent 66. In one or more other embodiments, the proximal bumper 26 can be substantially similar to the combination solder joint 52 and proximal marker 88 described above with reference to FIG. 1.

Further, in some embodiments, a portion of the stent 66 can be engageable with or disposed within a proximal mechanism and/or the proximal retaining member. In such embodiments, the stent 66 can be disengageable from the proximal mechanism and/or proximal retaining member by axially moving a sleeve and/or rotating the proximal bumper 26 via the proximal end 53*a* of the core wire 59. In other embodiments, however, the proximal bumper 26 can be an axial stent bumper that is coupled to the core wire 59 and configured to urge or bias the stent 66 in the distal direction via the proximal end 68.

In those embodiments where the marker band 26*a* of the proximal bumper 26 is made of platinum or another radiopaque material or substance visible through CAT scan, X-Ray, MM, or ultrasound technology, a user can be able to pinpoint the location and track the progression of the proximal end 68 of the stent 66 within the catheter 8 or blood vessel by determining the location of the proximal bumper 26.

The stent bumper(s) 62 can be spaced longitudinally along the core wire 59 and coupled thereto for mutual movement. Although three stent bumpers 62 are illustrated, more or fewer than three stent bumpers 62 can be used in the system 5, without departing from the scope of the disclosure. Moreover, the stent bumpers 62 can be equidistantly spaced or randomly spaced along the core wire 59, depending on the application. In some embodiments, one or more of the stent bumpers 62 can be shrink tubes coupled to the core wire 59 by shrinking the stent bumpers 62 directly onto the core wire 59. In other embodiments, one or more of the stent bumpers 62 are coupled to the core wire 59 via other attachment means including, but not limited to, mechanical fasteners, welding techniques, adhesives, combinations thereof, or the like.

The stent bumper(s) 62 can comprise a soft or compressible polymer or elastomer that is fixed to the core wire 59 and can form a generally cylindrical outer surface. The polymer or elastomer can overlie one or more metallic coils that are wound around and welded to the core wire 59. For example, two spaced coils of stainless steel or platinum-tungsten can be employed in the construction of a single bumper 62. To enhance flexibility the coils can have an open-pitch configuration, be welded to the core wire 59 only at the end points, and/or separated by a slight gap that is similar in size to the pitch employed in the coils. The polymer or elastomer can form a generally cylindrical outer surface along the portion that overlies the coil(s), and taper down toward the core wire 59 distal end proximal of the coil(s). The polymer or elastomer can comprise Pebax (e.g., Pebax 3533), PTFE, FEP, silicone, or other medical grade polymers or elastomers.

In its compressed state within the catheter 8, the stent 66 can underlie the sidewall of the catheter 8 and overlies the stent bumper(s) 62. Specifically, the inner surface 40*a* of the stent 66 can contact the outer radial surface of the stent bumpers 62, and the outer surface 40*b* of the stent 66 can contact the inner radial surface 17 of the catheter 8. In some embodiments, the stent bumpers 62 can be sized or otherwise configured to engage the inner surface 40*a* of the stent 66 sufficiently to exceed the coefficient of friction between the outer surface 40*b* of the stent 66 and the inner surface 17 of the catheter 8. As a result, the stent bumpers 62 can translate the stent 66 axially within the catheter 8 without the stent 66 binding against the inner surface 17 of the catheter 8. Moreover, this arrangement can enable the stent 66 to be resheathable, or to be drawn back within the catheter 8, as long as at least a portion of the stent 66 remains interposed between the inner surface 17 of the catheter 8 and one or more of the stent bumpers 62.

Additionally, in some embodiments, the core assembly can optionally comprise at least one expandable member. The expandable member can comprise one or more arms, radial members, or filaments that can move from a collapsed position to an expanded position. When moved to the expanded position, the expandable member can facilitate deployment of the stent. The expandable member can comprise a resilient, flexible material that can automatically or manually expand from the collapsed state. In some embodiments, the expandable member can comprise a shape memory material that expands when radially unrestrained by the elongate body.

The expandable member can be configured to slide and/or rotate relative to the core wire. The expandable member can be positioned at any of a variety of locations along the core wire.

For example, an expandable member(s) can facilitate initial expansion of one or more portions of the stent. In some embodiments, an expandable member can be positioned at a distal portion of the core assembly under a distal portion of the stent, such that upon exiting the microcatheter, the expandable member immediately self-expands under the stent and urges the stent towards an expanded position.

Further, an expandable member(s) can be used to ensure that the stent has fully deployed at all portions thereof. For example, when radially unrestrained by the elongate body or microcatheter, it is possible that a stent may have one or more portions that have not fully expanded into apposition with the vessel wall. In such situations, the expandable member(s) of the core assembly can be axially moved along and within the lumen of the stent, and thereby employed to push the non-expanded portion(s) of the stent radially outward into contact with the inner surface of the blood vessel.

In accordance with some embodiments, the expandable member can comprise a plurality of filaments that extend in a curvilinear manner. The expandable member can comprise an "onion-shaped" structure, an ellipsoid of revolution, a prolate spheroid, etc. Advantageously, embodiments having filaments in a "bell curve" shape can allow the expandable member to be urged both distally and proximally within a lumen of the stent ("brushed" or "brushing") without harming the framework of the stent or otherwise snagging with the stent or inner of the vessel. Various advantageous geometries can be provided that facilitate initial expansion of one or more portions of the stent that do not require proximal and distal movement. Thus, some embodiments can be provided that are suitable for initial expansion while others are suitable for brushing, and yet other embodiments can be provided that are suitable for both.

Further, the core assembly can comprise one or more blocking components for limiting axial and/or rotational movement of the at least one expandable member. The one or more blocking components can comprise at least one fixed blocking component and/or at least one movable blocking component. The blocking component(s) and the expandable member can interact or engage with each other in an axial direction or a rotational direction. The interaction between the blocking component(s) and the expandable member can thereby permit or limit certain types of motion of the expandable member.

The blocking component(s) can be formed separately from the core wire and/or integrally with the core wire (e.g., both being formed from a single piece of material). In embodiments having more than one blocking component, one blocking component can be formed separately from the core wire while another blocking component can be formed integrally with the core wire. Further, the shape and dimensions of the blocking component(s) can define a variety of geometries operative to provide a desired interaction with each other and/or with the expandable member.

For example, as illustrated in FIG. 2, the core assembly 57 can further include one or more optional expandable members 54 arranged at or near the distal end 53*b* of the core wire 59. Although embodiments illustrated and discussed herein refer to a single expandable member, two or more expandable members can be used in some embodiments. Further, the discussion of certain features can also be extended to multiple expandable members in such embodiments.

As illustrated in the embodiment shown in FIG. 2, the expandable member 54 can comprise one or more generally longitudinally arranged expandable struts extending from a proximal end 58*a* to a distal end 58*b*. In some embodiments, the struts can be self-expanding, such that the expandable member 54 can move on its own to an expanded configuration from a collapsed configuration. Therefore, in some embodiments, movement of the expandable member 54 to the expanded configuration can be automatic or self-expanding. For example, the struts can be heat set, preformed, or otherwise configured to expand from a collapsed state to an expanded state. The struts can form a shape that is generally spherical, bulbous, or otherwise radially extending from the core wire. Further, the struts can define a generally smooth outer profile for the expandable member 54 that can allow the expandable member 54 to be moved within the lumen and against the inner surface of the stent 66.

Referring still to the embodiment illustrated in FIG. 2, the expandable struts or members 54*a*, 54*b*, and 54*c* can extend from the core wire 59 into contact with an inner surface of the stent 66. In one or more embodiments, the expandable member 54 can be formed from a generally tubular structure (e.g., a hypotube) made of shape-memory or super-elastic materials, such as nitinol, or other resilient materials. The struts 54*a-c* can be laser-cut into a middle or central portion of the expandable member 54, and the proximal and distal ends 58*a, b* can therefore be short lengths of the uncut tubular structure. The members 54*a-c* can be configured to automatically or manually assume an expanded state (e.g., self-expand) when deployed out the distal end 19 of the catheter 8, or when unrestrained by the catheter. While disposed within the catheter 8, the members 54*a-c* are compressed against their natural disposition and consequently urge an overlying portion of the stent 66 radially outward. When unrestrained or otherwise expanded, however, each respective member 54*a-c* expands radially in various angular directions about the core wire 59.

The expandable member can be coupled to the core wire in a manner that permits relative movement therebetween as the core wire translates within the catheter and/or a blood vessel. According to some embodiments, one or both ends of the expandable member can be axially freely movable along the core wire. In some embodiments, at least one end of the expandable member can be formed with, bonded, fixed, constrained, or fixedly coupled relative to the core wire to permit limited movement or no movement of the end of the expandable member relative to the core wire.

For example, in some embodiments, the proximal end 58*a* can be secured relative to the core wire 59. In other embodiments, the distal end 58*b* can be secured relative to the core wire 59. In some embodiments, one of the ends of the expandable member 54 can be directly coupled to the core wire 59. Further, although the expandable member can have two ends that are each coupled to the core wire (whether slidably or fixedly), other embodiments can be configured such that the expandable member is coupled to the core wire at only a single end of the expandable member. Such embodiments can be configured such that the expandable member has a free end unconnected to the core wire that is resiliently movable relative to the core wire.

Figure 3A:
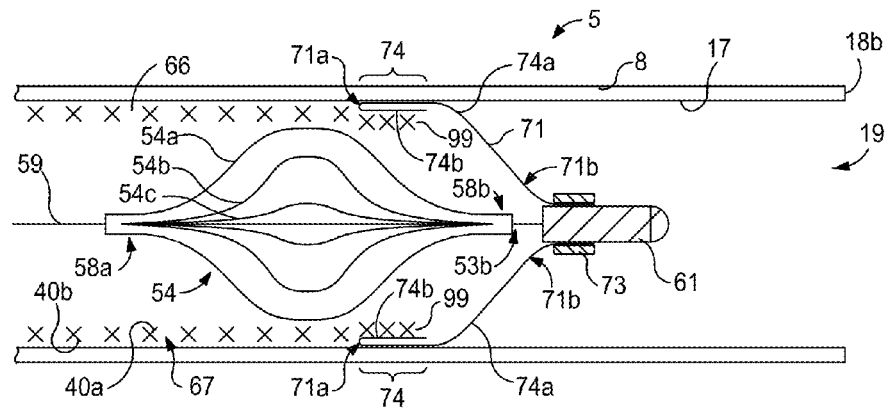
FIG. 3A illustrates an enlarged, cross-sectional view of the distal end of the stent delivery system of FIG. 2, according to one or more embodiments.
Figure 3B:
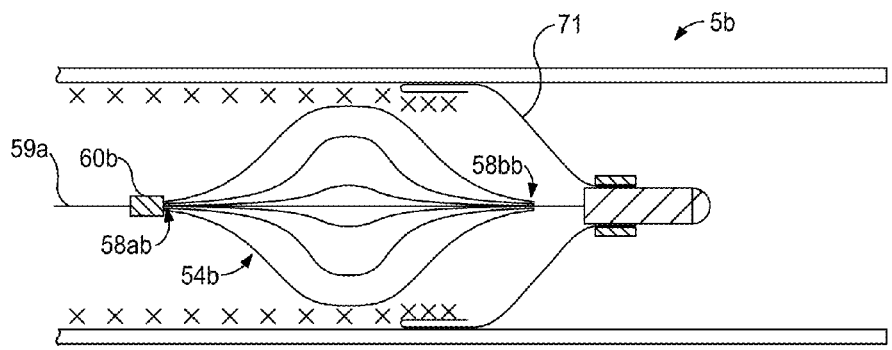
FIG. 3B illustrates an enlarged, cross-sectional view of the distal end of another embodiment of the stent delivery system of FIG. 2.

For example, as illustrated in the embodiment of the system 5*b* shown in FIG. 3B, one or more attachment means or coupling devices 60*b* can be used to secure the proximal end 58*ab* of the expandable member 54*b* to the core wire 59*b*. The coupling device 60*b* can comprise a mechanical fastener, shrink tubing, a weld, adhesives, heat bonding, combinations thereof, or the like, or an uncut proximal tubular portion of the hypotube which is cut to form the expandable member 54*b*. In some embodiments, the proximal end 58*ab* can be fixedly coupled with the core wire 59*b*, and the distal end 58*bb* of the expandable member 54*b* can remain free to move on and along the core wire 59*b*. As a result, as the struts of the expandable member 54*b* expand, the distal end 58*bb* can be free to slidably move along the core wire 59*b* toward the proximal end 58*ab*, thereby facilitating expansion or contraction of the expandable member 54*b*. In other embodiments, however, the expandable member 54*b* can be fixedly coupled to the core wire 59*b* at its distal end 58*bb* instead of at its proximal end 58*ab*, thereby allowing the proximal end 58*ab* of the expandable member 54*b* to remain free, and likewise longitudinally translate, as generally described above.

In accordance with some embodiments, the expandable member can be coupled to the core wire and positioned proximally of the proximal bumper 26. The expandable member can therefore be positioned outside of the stent lumen when the stent is in the collapsed configuration. Thus, while the expandable member may not assist in the initial expansion of the stent, the expandable member could be used as a dedicated mechanism that assists in fully expanding the stent after the stent has been released and initially expanded. In such embodiments, the expandable member could be inserted into the stent through the stent proximal end and moved within the stent lumen until all portions of the stent are fully expanded.

Additionally, in some embodiments, both ends of the expandable member can be axially and/or rotatably freely movable along and/or about the core wire. Thus, one or both of the ends of the expandable member can rotate and/or translate along the core wire. In such embodiments, the core wire can comprise one or more blocking structures operative to limit the axial and/or rotational movement of one or both of the ends of the expandable member.

The blocking structures can comprise one or more movable blocking structures and/or one or more fixed blocking structures. For example, a movable blocking structure can be configured to slide and/or rotate along the core wire. A fixed blocking structure can be axially and/or rotatably fixed relative to the core wire. The fixed blocking structure can be formed separately from the core wire and bonded or otherwise attached to the core wire. However, the fixed blocking structure can also be formed integrally with the core wire. Further, the distal tip of the core assembly can act as or be a fixed blocking structure (see FIG. 3D). In some embodiments, the movable blocking structure can interact with the fixed blocking structure and one or both of the ends of the expandable member to limit movement of the expandable member.

Figure 3C:
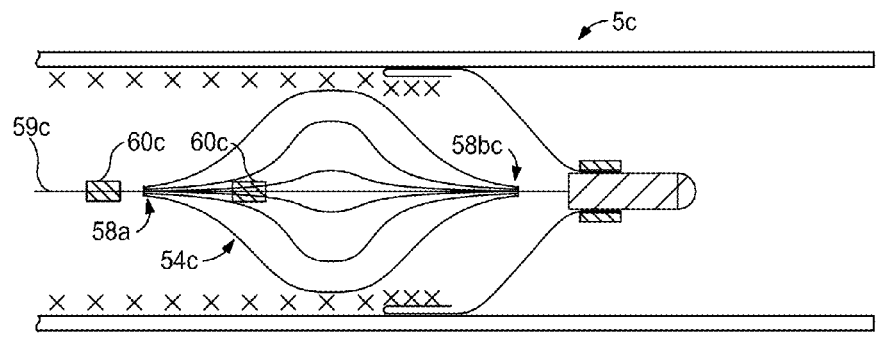
FIG. 3C illustrates an enlarged, cross-sectional view of the distal end of yet another embodiment of the stent delivery system of FIG. 2.
Figure 3D:
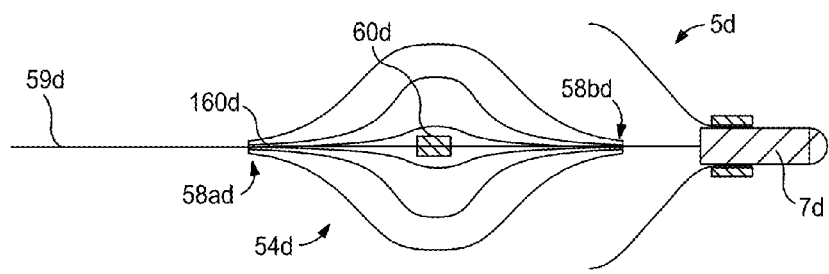
FIG. 3D illustrates an enlarged, cross-sectional view of the distal end of yet another embodiment of the stent delivery system of FIG. 2.
Figure 3E:
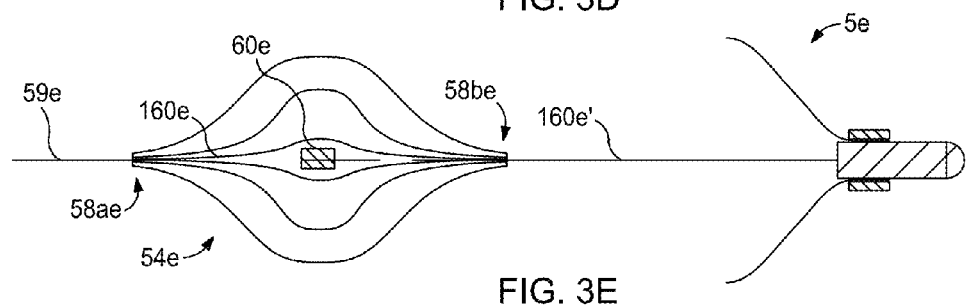
FIG. 3E illustrates an enlarged, cross-sectional view of the distal end of yet another embodiment of the stent delivery system of FIG. 2.
Figure 3F:
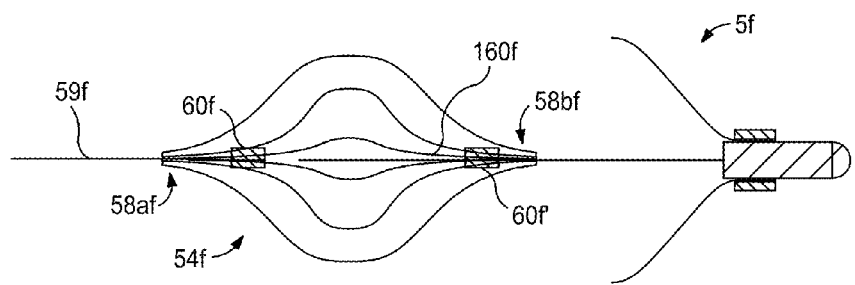
FIG. 3F illustrates an enlarged, cross-sectional view of the distal end of yet another embodiment of the stent delivery system of FIG. 2.
Figure 3G:
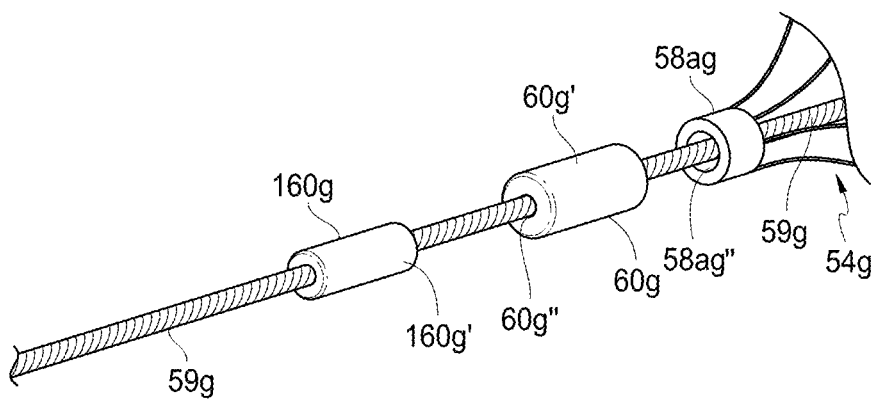
FIG. 3G illustrates a perspective view of the distal end of yet another embodiment of the stent delivery system of FIG. 2.

For example, as shown in FIG. 3G, a fixed blocking structure 160g can be rotatably and axially fixed relative to the core wire 59g. A movable blocking structure 60g can be disposed on the core wire 59g and permitted to freely rotate and move axially along the core wire 59g. Further, an end 58ag (which can be proximal and/or distal) of an expandable member 54g can also be rotatably and axially movable along the core wire 59g. As illustrated, the fixed blocking structure 160g can define an outer profile or cross-sectional profile 160g' that is greater than an inner profile or cross-sectional profile 60g" of the movable blocking structure 60g. Accordingly, an end surface of the fixed blocking structure 160g can be operative to contact a corresponding surface of the movable blocking structure 60g to prevent the movable blocking structure 60g from moving axially past the fixed blocking structure 160g. Thus, the fixed blocking structure 160g can serve as a limit of travel of the movable blocking structure 60g.

In addition, in some embodiments, the movable blocking structure 60g can define an outer cross-reference sectional profile 60g' that is greater than an inner profile or cross-sectional profile 58ag" of the end 58ag of the expandable member 54g. As such, an end surface of the movable blocking structure 60g can be operative to contact the end 58ag of the expandable member 54g and prevent the expandable member 54g from moving past the movable blocking structure 60g.

Further, in embodiments that use both a fixed blocking structure 160g and a movable blocking structure 60g, movement of the end 58ag of the expandable member 54g can be limited through indirect contact with the fixed blocking structure 160g.

In some embodiments, the movable blocking structure 60g can be disposed outside of the ends (or lumen) of the expandable member 54g. However, in other embodiments, the movable blocking structure 60g can be disposed inside or between the ends (or lumen) of the expandable member 54g. Further, one or more movable blocking structures can be used in some embodiments. Additionally, one or more fixed blocking structures can be used in some embodiments.

In some embodiments, both ends of the expandable member can be confined or limited to a length of travel. For example, in some embodiments, both ends can be positioned between a pair of blocking structures that are spaced at a minimum axial distance that is approximately equal to the length of individual struts of the expandable member. Accordingly, both ends of the expandable member could be axially movable until the expandable member is fully compressed or collapsed to permit the expandable member to be stowed within the lumen of the catheter. Further, one or more blocking structures can be placed between both ends of the expandable member, such that both ends can move axially in either direction, but are limited from further axial movement upon contact with the one or more blocking structures.

Further, some embodiments can be configured such that only one of the ends of the expandable member is confined or limited to a length of travel. For example, a first end of the expandable member can be positioned between the pair of blocking structures, such that the first end is constrained by the blocking structures while a second end of the expandable member is unconstrained and generally free to move.

Various configurations of the blocking structure(s) and the expandable member can be developed using the teachings disclosed herein. The following embodiments illustrate possible configurations, and shall not be considered to limit the disclosure herein.

Referring initially to embodiments illustrated in FIG. 3C, a system 5c is shown in which a pair of blocking members 60c are positioned on either side of the proximal end 58ac of the expandable member 54c. The blocking members 60c can be fixed relative to the core wire 59c. Thus, travel of the proximal end 58ac of the expandable member 54c can be limited to the space defined between the blocking members 60c. However, the distal end 58bc can be free to travel. Thus, the axial position of the distal end 58bc can be responsive to movement of the proximal end 58ac, compression of the expandable member 54c, and/or expansion of the expandable member 54c.

FIG. 3D illustrates an embodiment of a system 5d in which an expandable member 54d is slidable along a core wire 59d. The system 5d can comprise a fixed blocking member 160d and a movable blocking member 60d. The fixed blocking member 160d can define an outer profile or cross-section that is greater than an inner profile or cross-section of a lumen of the movable blocking member 60d, thus preventing the movable blocking member 60d from be able to pass or slide over fixed blocking member 160d.

The movable blocking member 60d can be disposed axially between the proximal and distal ends 58ad, 58bd of the expandable member 54d. The movable blocking member 60d can be configured to define an outer profile or cross-section that is greater than the inner profile of the lumens of the proximal and distal ends 58ad, 58bd of the expandable member 54d.

Further, in some embodiments, the lumen of the proximal end 58ad of the expandable member 54d can define a profile or cross-section that is greater than an outer profile or cross-section of the fixed blocking member 160d. Thus, although the proximal end 58*ad* can traverse or axially pass or slide over the fixed blocking member 160*d*, the proximal movement of the expandable member 54*d* can be limited upon contact between the fixed blocking member 160*d*, the movable blocking member 60*d*, and the distal end 58*bd* of the expandable member 54*d*. Further, distal movement of the expandable member 54*d* can be limited upon contact between the distal end 58*bd* of the expandable member 54*d* and the distal tip portion 7*d*.

FIG. 3E illustrates an embodiment of another system 5*e* in which an expandable member 54*e* is slidable along a core wire 59*e*. The system 5*e* can comprise a pair of fixed blocking members 160*e*, 160*e'* and a movable blocking member 60*e*. The movable blocking member 60*e* is disposed axially between the proximal and distal ends 58*ae*, 58*be* of the expandable member 54*e*. The fixed blocking members 160*e*, 160*e'* can define outer profiles or cross-sections that are greater than an inner profile or cross-section of a lumen of the movable blocking member 60*e*, thus preventing the movable blocking member 60*e* from be able to pass or slide over fixed blocking members 160*e*, 160*e'*.

The movable blocking member 60*e* can define an outer profile or cross-section that is greater than the inner cross section of the lumens of the proximal and distal ends 58*ae*, 58*be* of the expandable member 54*e*. Further, the lumen of the proximal end 58*ae* of the expandable member 54*e* can define a profile or cross-section that is greater than an outer profile or cross-section of the fixed blocking member 160*e*, and the lumen of the distal end 58*be* of the expandable member 54*e* can define a profile or cross-section that is greater than an outer profile or cross-section of the fixed blocking member 160*e'*.

Accordingly, in some embodiments, the proximal end 58*ae* can traverse or axially pass or slide over the fixed blocking member 160*e*, and the distal end 58*be* can traverse or axially pass or slide over the fixed blocking member 160*e'*. However, the proximal movement of the expandable member 54*e* can be limited upon contact between the fixed blocking member 160*e*, the movable blocking member 60*d*, and the distal end 58*bd* of the expandable member 54*d*. Further, the distal movement of the expandable member 54*e* can be limited upon contact between the fixed blocking member 160*e'*, the movable blocking member 60*e*, and the proximal end 58*ae* of the expandable member 54*e*.

FIG. 3F illustrates yet another embodiment of a system 5*f* in which expandable member 54*f* is slidable along the core wire 59*f*. In this embodiment, the system 5*f* can comprise a pair of movable blocking members 60*f*, 60*f'* and a single fixed blocking member 160*f* interposed between the movable blocking members 60*f*, 60*f'*. The fixed blocking member 160*f* can define an outer profile or cross-section that is greater than an inner profile or cross-section of a lumen of the movable blocking members 60*f*, 60*f'*, thus preventing the movable blocking members 60*f*, 60*f'* from be able to pass or slide over fixed blocking member 160*f*.

Further, as similarly noted with respect to the above embodiments, the movable blocking members 60*f*, 60*f'* can define outer cross sections that are greater than the inner profiles of the lumens of the proximal and distal ends 58*af*, 58*bf* of the expandable member 54*f*. Thus, proximal movement of the expandable member 54*f* can be limited upon contact between the distal end 58*bf* of the expandable member 54*f*, the movable locking structure 60*f*, and the fixed blocking structure 160*f*. Further, distal movement of the expandable member 54*f* can be limited upon contact between the proximal end 58*af* of the expandable member 54*f*, the movable locking structure 60*f*, and the fixed blocking structure 160*f*.

In accordance with some embodiments, the expandable member can be configured such that the size of the lumens of the proximal and distal ends can be configured to allow passage of some fixed blocking members while preventing the passage of other fixed blocking members. A proximal fixed blocking member can be sized larger than a lumen of a proximal end of the expandable member, such that the proximal fixed blocking member does not permit the expandable member to pass any further proximally once the proximal fixed blocking member contacts the proximal end of the expandable member. Additionally, the size of the lumen of the proximal end of the expandable member can also be smaller than one or more distal fixed blocking members disposed along the core wire, similarly preventing the proximal end of the expandable member from advancing any further distally once the proximal end of the expandable member contacts the given distal fixed blocking member.

However, the distal end of the expandable member can comprise a lumen that is larger than a distal fixed blocking member, such that the distal end of the expandable member can pass over the distal fixed blocking member, allowing the distal end of the expandable member to be generally unconstrained relative to one or more distal fixed blocking members.

Figure 4:
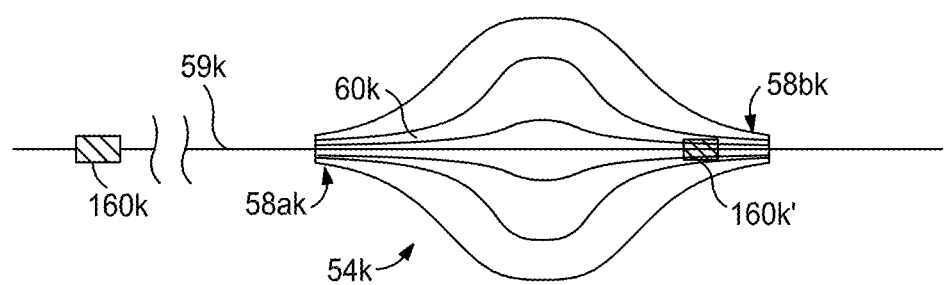
FIG. 4 illustrates an enlarged, cross-sectional view of an expandable member and bumpers positioned along a core wire, according to some embodiments.
Figure 5:
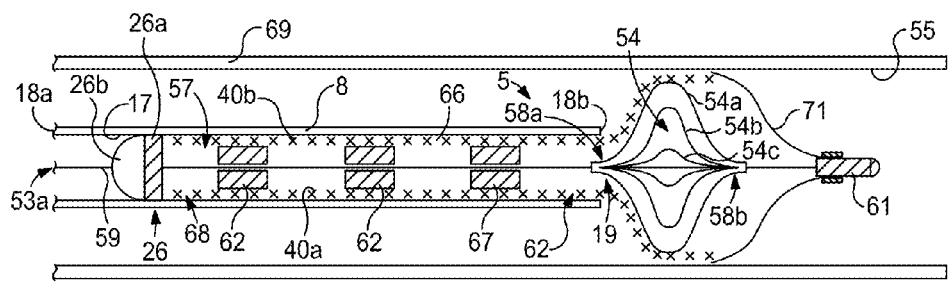
FIG. 5 illustrates a stent delivery system with a partially deployed stent, according to one or more embodiments.

For example, FIG. 4 illustrates an embodiment of a configuration comprising an expandable member 54*k*, a core wire 59*k*, and one or more fixed blocking members 160*k*, 160*k'*. As shown, the expandable member 54*k* can comprise a proximal end 58*ak* and a distal end 58*bk*. The proximal and distal ends 58*ak*, 58*bk* can each define lumens through which the core wire 59*k* can be slidably placed.

The expandable member 54*k*, in some embodiments, can slide relative to the core wire 59*k*. The length of travel of the expandable member 54*k* can be limited by the distance between the fixed blocking members 160*k*, 160*k'*. Further, the proximal and distal ends 58*ak*, 58*bk* of the expandable member 54*k* can move relative to each other based on the expansion of the expandable member 54*k*.

In some embodiments, the lumen of the distal end 58*bk* can define a diameter that is greater than a diameter of the fixed blocking member 160*k'*. However, the outer profile or shape of the fixed blocking member 160*k'* and the lumen of the distal end 58*bk* can comprise shapes other than circular.

In accordance with some embodiments, the lumen of the distal end 58*bk* can be sized to allow the fixed blocking member 160*k'* to pass therethrough. However, the lumen of the proximal end 58*ak* can be sized to prevent passage of the fixed blocking members 160*k*, 160*k'* therethrough. Accordingly, in some embodiments, the outside diameter of the fixed blocking members 160*k*, 160*k'* can be greater than the inside diameter of the lumen of the proximal end 58*ak*. Further, the inside diameter of the distal end 58*bk* can be greater than the outside diameter of the fixed blocking member 160*k'*. Thus, in this embodiment, the proximal end 58*ak* of the expandable member 54*k* can be pushed distally by the fixed blocking member 160*k* or pulled proximally by the fixed blocking member 160*k'* while the distal end 58*bk* will not constrain or be constrained by the fixed blocking member 160*k'*. In accordance with some embodiments, the blocking member can be configured to engage with the expandable member to allow the clinician to distally push the expandable member while engaging a distal end of the expandable member and/or to withdraw the expandable member while engaging a proximal end of the expandable member. Thus, the expandable member can be moved without axially compressing the expandable member, which could cause the expandable member to invert or become jammed inside of the stent lumen.

As noted herein, in some embodiments, the presence of one or more blocking members can allow the clinician to push and/or pull the core wire until the one or more blocking members interacts with an end of the expandable member, whereupon further pushing or pulling of the core wire allows the clinician to impart a pushing or pulling force on the expandable member. In such embodiments, with the interaction between the blocking member(s) and the expandable member, the system can be configured such that stent foreshortening during stent expansion does not force the expandable member distally beyond the stent distal end.

In accordance with an aspect of some embodiments is the realization that after the stent distal end is initially "landed" and contacts the vessel wall, subsequently expanded sections of the stent will axially foreshorten, thus causing the overall stent to axially foreshorten and draw or advance the unexpanded stent proximal end in a distal direction. While the unexpanded stent proximal end advances distally, the core wire will tend to also advance distally relative to the stent distal end. Thus, in some embodiments, in order to prevent the expandable member from being forced distally beyond the stent distal end, the system can be configured such that blocking members positioned along the core wire do not engage with the stent proximal end or the stent distal end to push the expandable member distally beyond the stent distal end during expansion of the stent.

For example, as noted above in FIG. 4, in some embodiments, the expandable member 54k can move axially along the core wire 59k, constrained by the interaction between the proximal end 58ak and the fixed blocking members 160k, 160k', but not constrained by the interaction between the distal end 58bk and the fixed blocking members 160k, 160k'. In such embodiments, the fixed blocking members can be placed along the core wire 59k such that the expandable member 54k is not pushed out of the stent distal end as the core wire 59k advances distally during stent expansion.

Accordingly, in some embodiments, the (proximal) fixed blocking member 160k can be positioned along the core wire 59k spaced sufficiently apart from the expandable member proximal end such that the fixed blocking member 160k will not contact or will only insubstantially contact the proximal end 58ak such that any contact does not urge the expandable member 54k out of the stent distal end.

For example, in the pre-deployment or collapsed state of the stent delivery system, the fixed blocking member 160k can be proximally spaced apart from the proximal end 58ak of the expandable member 54k by a first distance. The first distance can be about equal to or greater than the distance that the core wire will advance relative to the stent distal end during stent expansion or as the stent delivery system moves to the deployed state in which the stent is fully expanded and released from the stent delivery system. The first distance can be between about 2 mm and about 60 mm. In some embodiments, the first distance can be between about 5 mm and about 40 mm. Further, in some embodiments, the first distance can be between about 10 mm and about 30 mm.

In some embodiments, the expandable member 54k can be positioned within the stent lumen and the fixed blocking member 160k can be located proximal to or outside of the stent proximal end when the stent is in the collapsed position. In such an embodiment, the fixed blocking member 160k can be spaced apart from the stent proximal end such that when the stent expands and the core wire 59k and the fixed blocking member 160k advance, the fixed blocking member 160k will not force the expandable member 54k distally beyond the stent distal end.

Additionally, in some embodiments wherein a distal fixed blocking member (such as fixed blocking member 160k') is configured to engage with the stent distal end, the distal fixed blocking member can be spaced from the stent distal end at a second distance. Similar to the first distance mentioned above, the second distance can be between about 2 mm and about 60 mm. In some embodiments, the second distance can be between about 5 mm and about 40 mm. Further, in some embodiments, the second distance can be between about 10 mm and about 30 mm. Further, in some embodiments, the distal fixed blocking member can be located proximal to the stent proximal end when the stent is in the collapsed position and can be configured such that it passes through and does not engage the stent proximal end. Furthermore, in some embodiments, the distal fixed blocking member can be located distal to the stent proximal end when the stent is in the collapsed position.

Other embodiments disclosed herein that incorporate one or more (fixed and/or movable) blocking members, such as the embodiments illustrated in FIGS. 3B-G, can also be configured such that stent expansion does not force the expandable member distally beyond the stent distal end. In order to achieve this, a fixed blocking member(s) can be spaced at an offset that allows the fixed blocking member to be advanced distally without pushing the expandable member out of the stent distal end, as discussed similarly above with respect to the first and second distances.

In accordance with some embodiments, the blocking member(s) can be configured to engage with the expandable member to allow the clinician to distally push the expandable member while engaging a distal end of the expandable member and/or to withdraw the expandable member while engaging a proximal end of the expandable member.

For example, the embodiment illustrated in FIG. 3E illustrates a system in which the movable blocking member 60e is disposed between the proximal and distal ends 58ae, 58be of the expandable member 54e. The movable blocking member 60e is sized to have an outer cross-sectional profile that is greater than the inner cross-sectional profile of the proximal and distal ends 58ae, 58be, which thereby constrains movement of the movable blocking member 60e. When the movable blocking member 60e engages with either of the fixed blocking members 160e, the movable blocking member 60e will also engage with the expandable member 54e upon further movement of the core wire 59e in a given direction.

In operation, if the core wire 59e is pulled in a proximal direction, the fixed blocking member 58be can initially contact the movable blocking member 60e and, upon further proximal movement of the core wire 59e, the movable blocking member 60e will contact the proximal end 58ae of the expandable member 54e. Additional proximal movement of the core wire 59e will thus withdraw the expandable member 54e in a proximal direction. As this occurs, the proximal end 58ae of the expandable member 54e may tend to (at least initially) be moved proximally away from the distal end 58be, thus potentially and initially somewhat elongating the expandable member 54e. However, the expandable member 54e will not tend to be jammed, inverted, or otherwise deflected from an expanded shape that can be optimal for facilitating complete stent expansion.

Additionally, if the core wire 59e is pushed in a distal direction, the fixed blocking member 58ae can initially contact the movable blocking member 60e and, upon further distal movement of the core wire 59*e*, the movable blocking member 60*e* will contact the distal end 58*be* of the expandable member 54*e*. Additional distal movement of the core wire 59*e* will thus "push" the expandable member 54*e* in a proximal direction. As this occurs, the distal end 58*be* of the expandable member 54*e* may tend to (at least initially) be moved distally away from the proximal end 58*ae*, thus potentially and initially somewhat elongating the expandable member 54*e*. However, the expandable member 54*e* will not tend to be jammed, inverted, or otherwise deflected from an expanded shape that can be optimal for facilitating complete stent expansion.

In some embodiments, a fixed blocking member can be coupled to a core wire and can be sized such that an outer cross-sectional profile of the fixed blocking member is greater than an inner cross-sectional profile of the lumens of the proximal and distal ends of the expandable member. Thus, an embodiment having only a single blocking member can be provided that allows the expandable member to be pushed distally while engaging the expandable member distal end and withdrawn proximally while engaging the expandable member proximal end.

Accordingly, the blocking member(s) can engage with a distal end of the expandable member to push the expandable member distally and/or can engage with a proximal end of the expandable member to withdraw the expandable member proximally. Thus, in some embodiments, the expandable member can be moved proximally or distally without axially compressing the proximal and distal ends of the expandable member, which could cause the expandable member to invert or become jammed inside of the stent lumen.

Optionally, one or more of the fixed blocking members can be formed along the core wire as a protrusion or structure of the core wire itself. However, one or more of the fixed blocking structures can also be a distinct structure that is formed separately of and coupled to the core wire in a manner that prevents at least axial movement of the fixed blocking structure along the core wire. Thus, the term "fixed" in some embodiments can refer at least to axial fixation along the core wire, while optionally permitting rotational movement of the fixed blocking structure relative to the core wire.

Optionally, the fixed blocking member and the lumen can comprise one or more surface features, such as threads, protrusions, or recesses configured such that the lumen and the fixed blocking member can interact as the lumen passes over the fixed blocking member. Further, in embodiments where the fixed blocking member and the lumen do not pass over each other, the fixed blocking member and/or the lumen can comprise structures or other features that can interact with each other to fix the rotational position of the expandable member relative to the core wire.

Accordingly, the above-noted examples provide possible configurations that can limit the proximal and/or distal movement of the expandable member relative to the core wire. Embodiments can be provided in which the movable blocking structures are omitted and the inner profiles of the lumens of the proximal and distal ends of the expandable member are configured to correspond with an outer profile or cross-section of the fixed blocking member(s).

However, some embodiments, including those illustrated and discussed above, can comprise at least one floating or movable blocking structure that can interact with a fixed blocking structure and one or both of the ends of the expandable member to limit or control axial and/or rotational movement of the expandable member. Further, the inner and/or outer "cross-section" of the lumens and members discussed herein can define any of a variety of geometric shapes or profiles.

For example, a variety of profiles can be provided that have one or more longitudinally extending slits or grooves that can provide a keyed structure so as to limit rotational movement of the expandable member relative to the core wire, but to allow axial movement of the expandable member relative to the core wire. Additionally, a variety of profiles can be provided that provide a proximal and/or distal axial travel limit while allowing rotation of the expandable member relative to the core wire.

While only three struts 54*a-c* are specifically referenced in FIG. 2 (among the six depicted therein), it will be appreciated that more or fewer than three struts 54*a-c* can be employed, without departing from the scope of the disclosure.

For example, the expandable member 54 can include between 3 and 5 struts, between 5 and 10 struts, between 10 and 15 struts, between 15 and 20 struts, or 20 or more struts. Moreover, while the expandable member 54 is characterized or otherwise depicted as an expanded tube or "onion-shaped" structure, it can equally conform to other shapes and/or configurations in order to fit particular applications. Other such shapes and/or configurations can include an ellipsoid of revolution, a prolate spheroid, etc.

The core assembly 57 can further include a distal stent cover 71 configured to act as a bearing or reduce friction between the stent 66 (e.g., the distal portion or distal end 67 thereof) and the inner surface 17 of the catheter 8. As shown in the embodiment in FIG. 2, the core assembly 57 can be configured such that the distal stent cover 71 extends adjacent to or at least partially axially over the expandable member 54.

In some embodiments, the expandable member can be positioned along the distal end of the core assembly 57. The expandable member 54 is shown in FIG. 2 as being axially positioned adjacent to the distal end 67 of the stent 66. In particular, the expandable member 54 can be positioned inside of the distal end 67 of the stent 66 and inside of the proximal portion of the distal stent cover 71. Further, the expandable member 54 can extend beyond the distal end 67 of the stent 66 and into a space defined by the proximally extending proximal portion of the distal stent cover 71.

In some embodiments, the expandable member can be positioned along the proximal end of the core assembly 57. The expandable member can also be positioned between the proximal and distal ends of the core assembly. For example, the expandable member can be positioned between the proximal and distal ends 68, 67 of the stent 66. Further, in embodiments wherein two or more expandable members are used, each can be positioned at or between the proximal and distal ends of the core assembly.

The distal stent cover 71 can be made of a lubricious and/or hydrophilic material. In some embodiments, the distal stent cover 71 can be made of polytetrafluoroethylene, better known as TEFLON®, but can be made from other lubricious materials known by those skilled in the art, without departing from the scope of the disclosure. The distal stent cover can include a proximal portion 71*a* and a distal portion 71*b*. In some embodiments, the distal portion 71*b* of the distal stent cover 71 can be coupled to the tip coil 61 using, for example, a shrink tube 73 configured to shrink and capture a distal end of the distal stent cover 71 against the tip coil 61. In other embodiments, the distal portion 71*b* of the distal stent cover 71 is coupled to the tip coil 61 via other devices or attachment means, including, but not limited to mechanical fasteners, welding techniques, adhesives, heat bonding, combinations thereof, or the like. In yet other embodiments, the distal stent cover 71 (i.e., the distal portion 71b) is coupled or otherwise attached directly to the distal portion 53b of the core wire 59 itself using one or more of the devices or attachment means discussed herein.

The distal stent cover 71 can be manufactured or otherwise cut from a tube of the material selected for the distal stent cover 71. In some embodiments, the proximal portion 71a can be formed as strips cut from the tube, and the distal portion 71b can be an uncut length of the tube. Accordingly, the tubular distal portion 71b and the proximally extending strips of the proximal portion 71a can form a single, integral device or structure. The distal stent cover 71 can be a generally cylindrical or tubular structure formed by one or more strips or flaps of material coupled to the distal tip portion. For example, the distal stent cover 71 can be attached to the tip coil 61. In some embodiments, the tubular distal portion 71b can be shrunk onto or otherwise coupled to the tip coil 61 using mechanical fasteners, welding techniques, adhesives, heat bonding, combinations thereof, or the like, and the shrink tube 73 can be used, as described above. In yet other embodiments, the shrink tube 73 alone can be coupled to the tubular distal portion 71b to the tip coil 61.

The distal stent cover 71 can comprise a tube wherein the proximal portion 71a includes two or more semi-cylindrical or partially cylindrical strips or tube portions separated by a corresponding number of generally parallel, longitudinally oriented cuts or separations formed or otherwise defined in the sidewall of the tube. Therefore, when in the pre-deployment state, as shown in FIGS. 2-3, the proximal portion 71a can generally have the shape of a longitudinally split or longitudinally slotted tube interposed between the outer surface 40b of the stent 66 and the inner surface 17 of the catheter 8. The strips of the proximal portion 71a can collectively span substantially the entire circumference of the outer surface 40b of the stent 66 (e.g., where the cuts between the strips are splits of substantially zero width), or somewhat less than the entire circumference (e.g., where the cuts between the strips are slots having significant width). The strips of the proximal portion 71a can be of substantially uniform size; e.g., two strips spanning approximately 180 degrees each, three strips of approximately 120 degrees each, four strips of approximately 90 degrees each, etc. Alternatively, the strips can differ in angular sizing, without departing from the scope of the disclosure. In some embodiments, only two strips or tube portions are employed in the proximal portion 71a. The use of two strips facilitates fold-over or everting of the distal stent cover 71, as discussed in more detail below, while minimizing the number of free or uncontained strips in the blood vessel lumen and any potential for injuring the vessel by virtue of contact between a strip and the vessel wall.

At or near the distal end 67 of the stent 66, the proximal portion 71a of the distal stent cover 71 can be inverted or otherwise folded within itself, thereby creating a folded region 74 interposed between the outer surface 40b of the stent 66 and the inner surface 17 of the catheter 8. As illustrated, the folded region 74 defines an outer layer 74a and an inner layer 74b, where the outer layer 74a is adjacent the inner surface 17 of the catheter 8 and the inner layer 74b is adjacent the outer surface 40b of the stent 66. In some embodiments, the distal stent cover 71 can be configured to fold over itself, in a manner opposite to that shown in FIG. 3A, such that layer 74a would be the inner layer and layer 74b would be the outer layer. In other embodiments, the proximal portion 71a is not folded, inverted, or everted at all, when in the pre-deployment configuration.

In operation, the distal stent cover 71, and in particular the folded region 74, generally covers and protects the distal end 67 of the stent 66 as the stent 66 is axially translated within the catheter 8. The distal stent cover 71 can serve as a bearing or buffer layer that, for example, prevents the filament ends 99 of the stent 66 from contacting the inner surface 17 of the catheter 8, which could damage the stent 66 and/or catheter 8, or otherwise compromise the structural integrity of the stent 66. In some embodiments, ends of the folded region 74 can be inverted within the distal stent cover 71, such that the end of the distal stent cover 71 forms the inner layer/surface between the outer surface of the stent 66 and the distal stent cover 71. This can permit distal advancement of the core wire assembly through the catheter 8, while engaging the inner surface of the catheter 8, without unfurling. Since the distal stent cover 71 can be made of a lubricious material, the distal stent cover 71 can exhibit a low coefficient of friction that allows the distal end 67 of the stent 66 to translate or slide within the catheter 8 with relative ease. For example, the distal stent cover 71 can have a coefficient of friction of between about 0.02 and about 0.2. In some embodiments, the distal stent cover 71 can have a coefficient of friction of about 0.04. Accordingly, the distal stent cover 71 may be configured to provide a lubricious interface between the outer surface 40b of the stent 66 and the inner surface 17 of the catheter 8.

Referring generally to FIGS. 2-8, operation of a stent delivery system 5 is illustrated in accordance with aspects of some embodiments. Operation of some embodiments can be performed such that the catheter 8 is percutaneously introduced into a blood vessel 69 and advanced to a treatment site in the blood vessel 69, such as the site of an aneurysm (not shown). In some embodiments, the catheter 8 is guided to the treatment site using fluoroscopic imaging, in which one or more radiopaque markers (not shown) located on the distal portion 18b of the catheter 8 indicate a position of the catheter 8 in a fluoroscopic image. The catheter 8 can also be guided using other imaging techniques including, but not limited to, ultrasound and magnetic resonance imaging.

Additionally or alternatively, in some embodiments, the expandable member can comprise one or more radiopaque materials or portions to facilitate fluoroscopic imaging of the stent delivery system. For example, the expandable member can be fabricated from a radiopaque material or comprise one or more markers located on the proximal or distal ends thereof.

Once the catheter 8 is positioned at the treatment site 53, the core assembly 57 can be introduced into the catheter 8 and advanced distally toward the distal opening 19. FIGS. 2-3 depict the stent delivery system 5 with the stent 66, expandable member 54, and distal stent cover 71 in a pre-deployment configuration. While in this configuration, the stent 66, expandable member 54, and distal stent cover 71 can be advanced distally within the catheter 8 from a starting location (e.g., in a proximal portion of the catheter 8, which can be outside of the body of the patient) to a location within the distal portion of the catheter 8, at or near the distal end 18b thereof. This advancement can be achieved by applying a distally directed force to the core wire 59, which force can be transmitted to the stent 66 via the bumpers(s) 62. As the stent 66, expandable member 54, and distal stent cover 71 are so advanced, the proximal portion 71a of the distal stent cover 71 remains interposed between the outer surface 40b and/or distal end 67 of the stent 66 and the inner surface 17 of the catheter 8. Thus, the distal stent cover 71 can prevent the distal end 67 of the advancing stent 66 (e.g., the filament ends 99 thereof) from damaging, abrading, or gouging the catheter 8, and from thereby impeding progress of the stent 66 along the catheter 8. This can, in turn, prevent damage to the stent 66 such as by longitudinal compression resulting from high friction generated between the distal end 67 and the catheter 8 while distally directed force is applied to the proximal portions of the stent 66.

The distal end 67 of the stent 66 can be advanced beyond the distal portion 18b of the catheter 8 while the proximal end 68 of the stent 66 remains compressed within the catheter 8. As the distal end 67 of the stent 66 exits the distal opening 19, it can automatically expand, be expanded manually, or self-expand to an expanded configuration. In its expanded configuration, the outer surface 40b of the stent 66 can be "landed" or extend to and preferably lie mostly or completely adjacent to the inner surface 55 of the blood vessel 69. Thereafter, the stent 66 can be fully deployed at the site or resheathed and repositioned, if necessary.

During deployment, the stent 66 can contract axially as it expands radially within the blood vessel. In some embodiments, the axial foreshortening of both the stent 66 and the expandable member 54, and their respective radial expansions, can cause the strips or tube portions of the proximal portion 71a (FIG. 3A) of the distal stent cover 71 to separate and move radially outward, disengaging from contact with the stent 66. In one or more embodiments, as the distal stent cover 71 moves and/or disengages from the stent, it unfurls or otherwise unravels from its folded configuration (FIG. 3A). Once the distal stent cover 71 withdraws or otherwise unravels, it may no longer cover the distal end 67 of the stent 66. Instead, the distal stent cover 71 may be left coupled to the tip coil 61 and its free ends may be generally unconstrained within the blood vessel 69.

Figure 8:
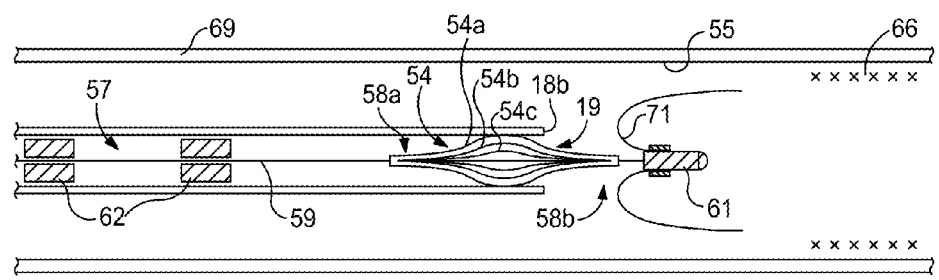
FIG. 8 illustrates an expandable member being resheathed into an elongate member or catheter, according to one or more embodiments.
Figure 9:
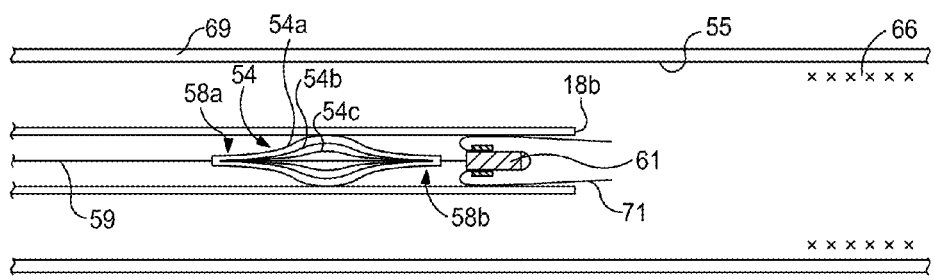
FIG. 9 illustrates a further progression of the resheathing process of the stent delivery system, according to one or more embodiments.

In some embodiments, such as shown in FIG. 8, if the distal stent cover 71 has unfurled, the distal stent cover 71 can be configured to entirely invert or fold back over itself as the wire 59 is drawn proximally. Thus, the distal stent cover 71 can be flexible and be able to be proximally withdrawn into the catheter to allow the core assembly (including the stent) to be resheathed or removed through the catheter. Thus, this can prove beneficial when the core assembly is withdrawn into the catheter after the stent has been deployed, which can allow for another core assembly (with an additional stent) to be introduced through the catheter to permit "telescoping" or placement of multiple stents without having to remove the catheter. As can also be appreciated, the flexibility of the distal stent cover 71 can also prove beneficial when the initial deployment site of the stent 66 is incorrect or otherwise has to be relocated to properly cover the treatment site of interest. Accordingly, in some embodiments, the stent 66 can be partially deployed, resheathed, and relocated multiple times as needed in order to ensure that the stent 66 is properly deployed in the correct location for best use.

Figure 6:
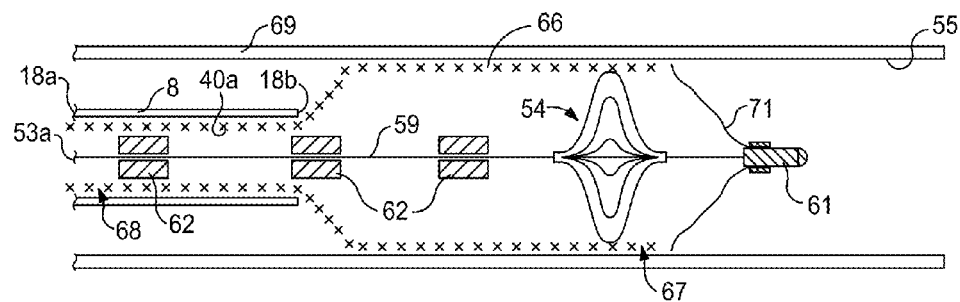
FIG. 6 illustrates a stent delivery system with a partially deployed stent, according to one or more embodiments.

For example, referring to FIG. 6, after initially "landing" the stent 66 in the blood vessel, in order to deploy the remaining portions of the stent 66 in the blood vessel 69, the catheter 8 can be retracted further proximally relative to the stent 66. As the catheter 8 is retracted, the released portions of the stent 66 can be expanded (automatically or manually) to contact the inner surface 55 of the blood vessel 69. In some embodiments, before the stent 66 is fully deployed into the blood vessel 69, and before the stent bumper(s) 62 has passed distally out of the catheter 8, the stent 66 can be retracted or otherwise resheathed back into the catheter 8. As the core wire 59 is retracted proximally, the one or more stent bumpers 62, which can still be in contact with, urged, or biased against the inner surface 40a of the stent 66, can grip the stent 66 to facilitate moving it proximally and back into its compressed configuration within the catheter 8.

For example, to resheath the core assembly 57 within the catheter 8, the core wire 59 can be pulled proximally while the catheter 8 remains stationary. As the core wire 59 moves proximally, if the core assembly 57 has any stent bumpers 62, they can be reintroduced into the catheter 8. Once the expandable member 54 reaches the distal opening 19, the struts 54a-c contact the distal portion 18b of the catheter 8 and are thereby forced back into their compressed configurations. As discussed above, the proximal and/or distal ends 58a, 58b can be freely axially movable along the core wire 59. Thus, the proximal and/or distal ends 58a, 58b can translate proximally and/or distally along the core wire 59 to facilitate compression or contraction of the expandable member 54. Specifically, in some embodiments, if the proximal end 58a is fixed relative to the core wire 59, the contact between the expandable member 54 and the catheter 8 can force the distal end 58b of the expandable member 54 to slide distally along the core wire 59 and thereby axially elongate and collapse or compact the expandable member 54 for reinsertion in the catheter 8.

In some embodiments, the expandable member 54 can facilitate the initial expansion and/or the subsequent or final expansion of the stent. For example, the expandable member can facilitate the initial expansion when the distal end of the stent is "landed" at the desired location. Further, after the stent is completely released from the core assembly, the expandable member can be used to urge partially expanded portions of the stent towards a fully expanded configuration by engaging the inner surface of the stent.

As discussed herein, in some embodiments, after the expandable member has exited the catheter, the expandable member can move from the collapsed position toward the expanded position. For example, the distal end and the proximal end of the expandable member can converge toward each other which allows the struts to expand radially. As discussed herein, some embodiments of the expandable member can comprise resilient struts or configuration that causes the expandable member to move to a radially expanded shape when outside of the catheter 8. In some embodiments, one or both of the proximal and distal ends 58a, 58b of the members 54a-c of the expanding member 54 can slide or otherwise translate along the core wire 59 to facilitate radial expansion of the expanding member 54. In embodiments wherein the proximal end 58a is fixed, the distal end 58b can contract proximally (i.e., converge axially toward the fixed proximal end 58a). These movements can cause the expandable member 54 to be axially contracted or foreshortened and radially expanded.

After the expandable member has expanded and/or while it expands, the expandable member 54 can cause at least a portion of the stent 66 to expand. For example, the expandable member 54 can cause at least a portion of the stent 66 to expand by expanding and engaging the inner surface of the stent 66. For example, if the expandable member is positioned adjacent to the distal end of the stent, the expandable member can facilitate expansion of the distal end of the stent to "land" the stent in the vessel. The expandable member can be used to help achieve consistent results of the system and provide full initial expansion of the stent within the blood vessel. For example, as the expandable member 54 exits the distal opening 19 of the catheter 8 along with the stent 66 during deployment, it can expand automatically, be expanded manually, or self-expand to its natural, expanded configuration. According to some embodiments, the struts can be configured such that spring forces in each of the struts 54a-c can tend to facilitate to the expansion of the distal end 67 of the stent 66. Accordingly, the expandable member 54 can facilitate a more complete initial expansion of the distal end 67 of the stent 66 into apposition with the vessel, thereby assisting in the initial anchoring of the distal end 67 of the stent 66. This also results in better wall apposition, such that an increased amount of friction is generated against the inner surface 55 of the blood vessel 69 by the stent 66. In some embodiments, increasing the friction force between the blood vessel 69 and the stent 66 can allow the user to strategically expand the remaining portions of the stent 66. Further, other portions of the stent (e.g., central portions, proximal portion, etc.) can be initially expanded using an expandable member. As noted above, more than one expandable member can be used in some embodiments, which can be employed to facilitate initial and/or subsequent or final expansion of the stent.

The expandable member can facilitate not only initial expansion upon deployment, but can also be passed along the lumen of the deployed stent to force open portions of the stent that may not have deployed fully. Thus, subsequent to the initial deployment, unsheathing, or release of the stent from the core wire, the expandable member can be passed axially along the lumen of the stent to tend to urge open any portions of the stent that did not expand into apposition with the walls of the vessel.

Figure 7:
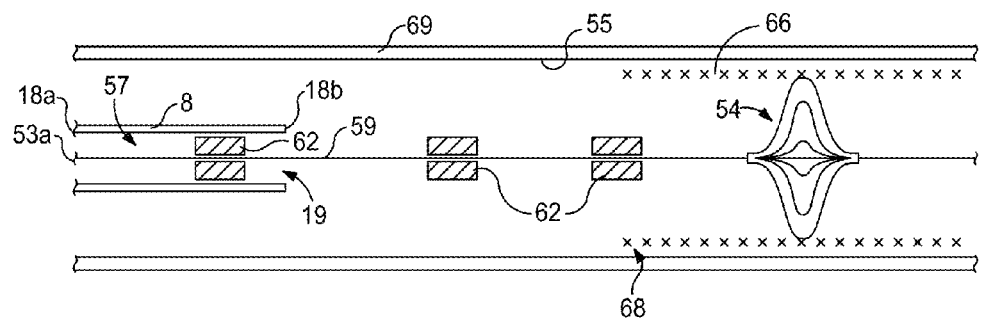
FIG. 7 illustrates a stent delivery system with a fully deployed stent, according to one or more embodiments.

For example, referring to the embodiment in FIG. 7, once the stent 66 is fully deployed within the blood vessel 69, the expandable member 54 can be used to ensure that every portion of the stent 66 is fully engaged with the inner surface 55 of the blood vessel 69. In some embodiments, the stent 66 can provide structural support to the vessel wall 55 to strengthen the blood vessel 69 and prevent or reduce the likelihood of reclosure. In some embodiments, the expandable member 54 can be translated axially back and forth within the deployed stent 66, continuously urging or biasing the inner surface 40a of the stent 66, such as in the use of a mandrel-type device. Using the radial spring force of the expandable member 54, any sagging or unapposed portions of the stent 66 can be pressed or forced into proper engagement with the blood vessel 69 as the expandable member 54 translates along the lumen of the stent 66.

Referring to FIGS. 7 and 8, after the stent 66 is fully deployed in the blood vessel 69, the catheter 8 and core assembly 57 can be withdrawn from the blood vessel 69 or otherwise retracted out of the vasculature of the patient. In some embodiments, the catheter 8 and the core assembly 57 can be removed separately from the blood vessel 69. In other embodiments, however, the core assembly 57 can be resheathed back into the catheter 8 and removed with the catheter 8. As also noted, the core assembly 57 can be easily withdrawn through the catheter 8 by itself (with the catheter 8 remaining in place) after stent deployment to facilitate "telescoping" or to reduce overall rigidity of the catheter assembly, such that the catheter can be more flexible when being withdrawn from the vessel.

The apparatus and methods discussed herein are not limited to the deployment and use of an occluding device within any particular vessels, but can include any number of different types of vessels. For example, in some aspects, vessels can include arteries or veins. In some aspects, the vessels can be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the stent delivery systems disclosed herein can be deployed within superthoracic vessels. The suprathoracic vessels can comprise at least one of intracranial vessels, cerebral arteries, and/or any branches thereof. For example, the suprathoracic vessels can comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels can also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels can also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels can also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels can also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels can comprise the aorta or branches thereof. For example, the intrathoracic vessels can comprise at least one of an ascending aorta, a descending aorta, an arch of the aorta, and/or branches thereof. The descending aorta can comprise at least one of a thoracic aorta, an abdominal aorta, and/or any branches thereof. The intrathoracic vessels can also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels can also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels can also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels can comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels can also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels can comprise at least one of humeral arteries, a transverse cervical artery, a suprascapular artery, a dorsal scapular artery, and/or branches thereof. The lateral thoracic vessels can also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, a catheter, such as that described in U.S. patent application Ser. No. 12/731,110, which was filed on Mar. 24, 2010, and which incorporated herein by reference in its entirety, can be used to deliver a stent delivery system. The delivery system can include an expandable occluding device (e.g., stent) configured to be placed across an aneurysm that is delivered through the distal portion of the catheter, out a distal tip, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

The apparatus and methods discussed herein are not limited to the deployment and use of an occluding device or stent within the vascular system but can include any number of further treatment applications. Other treatment sites can include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component, or method step is intended to be dedicated to the public regardless of whether the element, component, or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art can be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A stent delivery system, comprising:
   an elongate body having a lumen extending from a proximal portion to a distal portion of the body, the distal portion being configured to extend within a blood vessel;
   a stent expandable from a compressed configuration, sized to be received within the elongate body lumen, to an expanded configuration, the stent having a lumen and an inner surface extending from a proximal end to a distal end of the stent;
   a core wire configured to extend through the elongate body lumen and the stent lumen and having a distal region;
   a distal stent cover extending proximally from the distal region of the core wire and interposed between an outer surface of the stent and an inner surface of the elongate body;
   a self-expanding member disposed along the core wire distal region, the self-expanding member comprising first and second end portions, the first and second end portions each comprising lumens through which the core wire passes to enable the self-expanding member to be rotatably and slidably movable relative to the core wire, the self-expanding member being configured to facilitate the expansion of at least a portion of the stent to the expanded configuration by expanding and engaging the stent inner surface; and a fixed blocking member fixed to the core wire between the first and second end portions of the self-expanding member, the fixed blocking member having an outer cross-sectional profile greater than inner cross-sectional profiles of the apertures of the first and second end portions of the self-expanding member to limit axial movement of the first and second end portions along the core member upon contact with the fixed blocking member.

2. The system of claim 1, further comprising a movable blocking member being slidable along the core wire relative to the fixed blocking member, the fixed blocking member defining an outer cross-sectional profile that is sized greater than an inner cross-sectional profile of a lumen of the movable blocking member, the movable blocking member defining an outer cross-sectional profile that is sized greater than an inner cross-sectional profile of a lumen of the first end portion of the self-expanding member, the movable blocking member being disposed between the first end portion of the self-expanding member and the fixed blocking member, such that the first end portion of the self-expanding member is blocked from sliding past the movable blocking member and the fixed blocking member.

3. The system of claim 1, further comprising a movable blocking member.

4. The system of claim 1, further comprising a second fixed blocking member and a movable blocking member.

5. The system of claim 1, wherein the self-expanding member comprises a plurality of filaments.

6. The system of claim 1, wherein the self-expanding member comprises a shape memory material.

7. The system of claim 1, wherein the self-expanding member self-expands when radially unrestrained by the elongate body.

8. The system of claim 1, wherein the distal stent cover comprises a folded region having (a) an outer layer configured to be urged against the inner surface of the elongate body and (b) an inner layer configured to contact the outer surface of the stent.

9. The system of claim 8, wherein the folded region is an inverted section of the distal stent cover where the distal stent cover folds within itself.

10. The system of claim 1, wherein the distal stent cover is coupled to the core wire.

11. The system of claim 1, wherein the distal stent cover is formed by one or more flaps of material.

12. The system of claim 1, wherein the distal stent cover comprises a lubricious material.

13. A stent delivery system, comprising:

a core wire having a distal region;

a distal stent cover extending proximally from the distal region of the core wire, the distal stent cover configured to be disposed over an outer surface of a stent;

a self-expanding member disposed along the core wire distal region, the self-expanding member comprising first and second end portions that are each axially slidable along the core wire, wherein the self-expanding member can expand from a collapsed configuration to an expanded configuration upon axial convergence of the first and second end portions;

a fixed blocking member coupled to the core wire between the first and second end portions of the self-expanding member, the fixed blocking member limiting axial movement of the self-expanding member along the core member upon contact with the fixed blocking member; and an elongate body having proximal and distal portions and a lumen extending between the proximal and distal portions, wherein the core wire extends within the elongate body lumen.

14. The system of claim 13, wherein the blocking member limits axial movement of both the first and second end portions along the core member.

15. The system of claim 13, further comprising a movable blocking member being slidable along the core wire relative to the fixed blocking member.

16. The system of claim 15, wherein the movable blocking member comprises a lumen having an inner cross-sectional profile that is sized less than an outer cross-sectional profile of the fixed blocking member, the fixed blocking member limiting movement of the movable blocking member along the core wire.

17. The system of claim 16, wherein the first and second end portions each comprise a lumen, wherein the first end portion lumen has a first inner cross-sectional profile greater than a second inner cross-sectional profile of the second end portion lumen and the outer cross-sectional profile of the fixed blocking member, and wherein the movable blocking member comprises an outer cross sectional profile greater than the first inner cross-sectional profile to limit movement of the first end portion relative to the fixed blocking member.

18. The system of claim 13, wherein the first and second end portions each comprise a lumen, wherein the first end portion lumen has a first inner cross-sectional profile greater than a second inner cross-sectional profile of the second end portion lumen and an outer cross-sectional profile of the fixed blocking member.

* * * * *